United States Patent [19]

Cameron et al.

[11] Patent Number: 4,717,385
[45] Date of Patent: Jan. 5, 1988

[54] SURGICAL TUBE ANCHORING DEVICE AND METHOD FOR USING SAME

[75] Inventors: Pamela E. Cameron, Framingham; Esther F. Borrelli, Cambridge, both of Mass.

[73] Assignee: The Beth Israel Hospital Association, Boston, Mass.

[21] Appl. No.: 939,276

[22] Filed: Dec. 10, 1986

Related U.S. Application Data

[63] Continuation of Ser. No. 722,354, Apr. 12, 1985, abandoned.

[51] Int. Cl.⁴ .............................................. A61M 27/00
[52] U.S. Cl. .............................. 604/174; 128/DIG. 26; 285/194
[58] Field of Search ............... 604/174, 178, 179, 180, 604/175, 176, 177, 326, 331, 338, 339; 128/DIG. 26; 285/158, 194

[56] References Cited

U.S. PATENT DOCUMENTS

| | | | |
|---|---|---|---|
| 2,133,130 | 10/1938 | Buchstein | 128/DIG. 26 |
| 2,362,160 | 11/1944 | Robertson | 285/158 |
| 2,555,292 | 5/1951 | Poupitch | 285/194 |
| 2,586,940 | 2/1952 | Graham | 128/DIG. 26 |
| 2,927,807 | 3/1960 | Campbell | 285/158 |
| 3,138,158 | 6/1964 | Gordon et al. | 128/DIG. 26 |
| 3,422,817 | 1/1969 | Mishkin et al. | 128/DIG. 26 |
| 3,682,180 | 8/1972 | McFarlane | 128/350 |
| 3,683,911 | 8/1972 | McCormick | 128/214 |
| 3,893,446 | 7/1975 | Miller | 128/2 |
| 4,221,215 | 9/1980 | Mandelbaum | 128/155 |
| 4,223,671 | 9/1980 | Muto | 128/DIG. 26 |
| 4,261,363 | 4/1981 | Russo | 128/350 |
| 4,392,854 | 7/1983 | Ibach | 128/DIG. 26 |
| 4,435,174 | 5/1984 | Redmond et al. | 128/DIG. 26 |
| 4,519,793 | 5/1985 | Galindo | 128/DIG. 26 |

FOREIGN PATENT DOCUMENTS

1181139 10/1957 France .

OTHER PUBLICATIONS

Journal of Enterostonal Therapy, vol. 10, No. 3, May/-Jun. (1983), pp. 108–110.
Clinics in Gastroenterology, vol. II, No. 2, May 1982, pp. 345–350.
American Journal of Nursing, Jul. 1983, pp. 1030–1033.

Primary Examiner—Stephen C. Pellegrino
Attorney, Agent, or Firm—Lorusso & Loud

[57] ABSTRACT

A tube anchoring device for anchoring gastrostomy and similar surgical tubing, for use in conjunction with a flanged pectin and polymethylcellulose wafer where, in one embodiment, the tube anchoring device comprises a tube, for receiving the surgical tubing, having at one end at least three radially projecting legs, designed to extend to and snap under the flange of the wafer, thereby releasably and painlessly securing the surgical tube in a manner that also facilitates easy inspection and cleaning of the incision and minor repair of the wafer without removal of the anchoring device.

27 Claims, 5 Drawing Figures

SURGICAL TUBE ANCHORING DEVICE AND METHOD FOR USING SAME

This is a continuation of U.S. application No. 722,354, filed Apr. 12, 1985, now abandoned.

BACKGROUND OF THE INVENTION

This invention relates generally to surgical appliances and more specifically to a device for anchoring various types of surgical tubes, such as gastrostomy tubes painlessly, efficiently and economically.

Generally, patients who are unable to eat after having undergone certain surgical procedures, or who are unable to eat due to certain medical conditions, are supplied nutrients through a tube known as a "gastrostomy tube." It is necessary to anchor the gastrostomy tube, so that it does not pull out of the patient while the patient moves, or is moved during bathing, sheet changing, etc. Presently, practitioners use several methods to keep the tube from pulling out of the body. In each case, the tube is inserted into the stomach through an incision in the abdomen made by a procedure known as a "gastrostomy". To prevent the tube from pulling out of the body, a Foley (balloon), Malecot (batwing) or Pezzar (mushroom) catheter is inserted. Each of these devices is a unitary tube/catheter device.

It is also necessary to minimize relative movement between the tube and the incision site, because any movement causes ulceration of the site. The tube may still, however, flop around, because it is not confined in its inclination to the body. Prior to our invention, certain methods have been used. Each of those methods, described below, has drawbacks. All of the methods described below, in addition to our method, aim to secure the tube against side to side movement in addition to movement out of the patient's body.

One method used is to wrap a substantial amount of suture thread around the tube, forming a collar several inches from the incision. Suture strands are then anchored to the tube, by looping and tieing under the collar. The other end of each suture strand is then sutured to the patient's skin. This procedure is repeated at several locations around the circumference of the tube. Afterwards, the tube is taped to the skin several inches beyond the point of attachment of the sutures. The result is that the tube is secured in an upright position, resembling a radio transmission tower secured by guy wires, or the support structure of a tent. This method is painful and irritating to the patient, whose skin is constantly being tugged this way and that by the sutures piercing it.

Another method incorporates a plastic, stepped, accordian pleated sleeve and a pectin and polymethylcellulose wafer of the type used as part of a wafer and pouch system for containing effluent after surgical diversion of the intestine or bladder, in procedures such as nephrostomies. The tube/catheter unit is inserted into the body through the incision and anchored by activating the catheter as described above. Next, the tube is fed through the sleeve. The narrow opening of the sleeve faces away from the body and the wide end touches the body. The pectin wafer is placed over the sleeve, with the tube passing through a round hole in the center of the wafer. The sleeve is intended to secure the tube, but in practice, the sleeve is too flexible to provide the support necessary to immobilize the tube. Further, it is impossible to inspect or clean the incision site, without removal of the anchoring device, because it is covered by the pectin wafer and plastic sleeve. Cleaning is very important because of the risk of infection. Further, secretions trapped under the wafer irritate the skin.

Another method has been discussed using a pectin wafer of the type described above fitted with a flange (of the type sold by Squibb and Company under the trade name "Stomahesive Wafer with Sur-Fit Flange"), using a piece of durable suture and the screw-on cap of a baby bottle, having a hole in its face. The wafer is applied with the tube protruding through the opening. One inch above the incision, a length of 1-0 silk suture is tied to the tube tightly enough so that it will not slide. The thread is positioned so that it lies along the surgical tube to the center of the wafer and then out across the rim of the flange. The tube is passed through the hole in the baby bottle lid which is then snapped inside the flange, with the thread secured between the edge of the lid and the rim of the flange. The suture facilitates removal of the bottle lid, for access to the insertion site for inspection, cleaning and reinforcement of the wafer as it erodes. This method does not provide sufficient vertical support of the tube and requires the step of tieing and positioning the thread. The incision is not visible or accessible for cleaning without removing the bottle lid. Due to the tenderness of the site, any unnecessary movement and irritation is to be avoided.

Finally, a method similar that described above with respect to the bottle lid, employs a baby bottle nipple. This method has been described in the JOURNAL OF ENTEROSTOMAL THERAPY, Vol. 10, pp. 108-110 (1983). According to this method, the wafer is applied as above, and the tube is threaded through a nipple with the end snipped off. A convex insert ring of an appropriate size fits concentric with the nipple, and anchors the nipple to the flange, by snapping under the flange. The nipple then supports the tube. A drawback of this method are that the nipple is too flexible to support the tube. Further, it is not possible to examine and clean the incision site with the nipple in place. Finally, the flexible nipple and concentric ring assembly is complicated to install and remove.

Among the several objects of our invention is to provide an apparatus for the secure support of a gastrostomy or similar tube, without causing unnecessary pain to the patient. Another object of the invention is to provide such a support which is easy to install and remove, and which permits cleaning of the incision site without removal of the device. Another object of the invention is to provide such a support which permits inspection of the insertion site while the support device is in place. Yet another object of the invention is to provide a system of securing gastrostomy or similar tubes, which system may be easily adapted to secure tubes of various sizes and shapes. A final object is to provide a tube anchoring device and system simple to use that family members can attend to this aspect of the patient's care at home.

SUMMARY OF THE INVENTION

Our invention constitutes a painless, stable easy to use device for the securing of gastrostomy and other similar surgical tubes. The invention consists of an anchoring fixture specifically designed to hold the tube and snap into and out of a flange attached to a pectin wafer such as has been described above. The preferred embodiment of the invention comprises a split tube made from polycapralactone, or some other suitable thermoplastic material, having at least three legs extending from one end, like the legs of a spider. The legs are of the proper length and resilience so that they may snap under the flange of the wafer, which will secure the legs and the connected plastic tube against movement. The legs may also be snapped out from under the flange to facilitate cleaning and repair of the wafer. The legs are shaped so that while in place, the body of the tube rests a distance away from the incision, so that the incision may be visually inspected. Further, access for cleaning and small instruments is provided between the legs of the apparatus. The anchor tube is cut along its length so that the surgical tube may be fitted into the tube from the side, without any need to thread the surgical tube through the fixture tube in its long direction. The anchor is safe and painless for the patient, and easy to install and remove for the attending medical staff.

DETAILED DESCRIPTION OF THE PREFERRED EMBODIMENT

Figure 1:
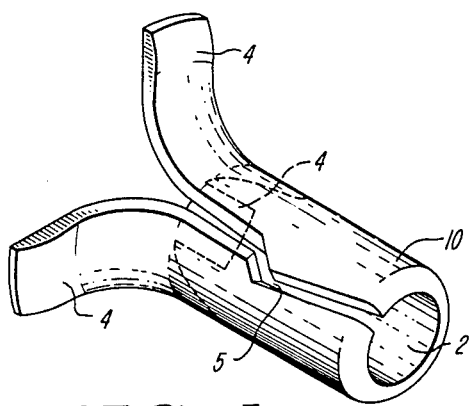
FIG. 1—FIG. 1 is an isometric view of one embodiment of our invention.
Figure 5:
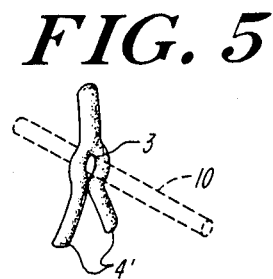
FIG. 5—FIG. 5 is an isometric view of the embodiment of FIG. 4.

Our invention will be more easily understood with reference to the Drawing. FIG. 1 shows a preferred embodiment of our device, free-standing. The surgical tube passes through the cavity (2) of the anchor device. The legs (4) of the anchor device snap into the ring of the flange of the "Sur Fit" type pectin and polymethylcellulose wafer (5), the configuration of which can be most easily seen in FIG. 3. In FIG. 1, the third leg of the support tube is shown in phantom.

The pectin wafer (14) has a hole (16) at its center, concentric with a flanged ring (18) that is bonded to one side of the wafer (20). The other side of the wafer (22) is provided with adhesive, covered by a removable sheet of backing paper.

Figure 2:
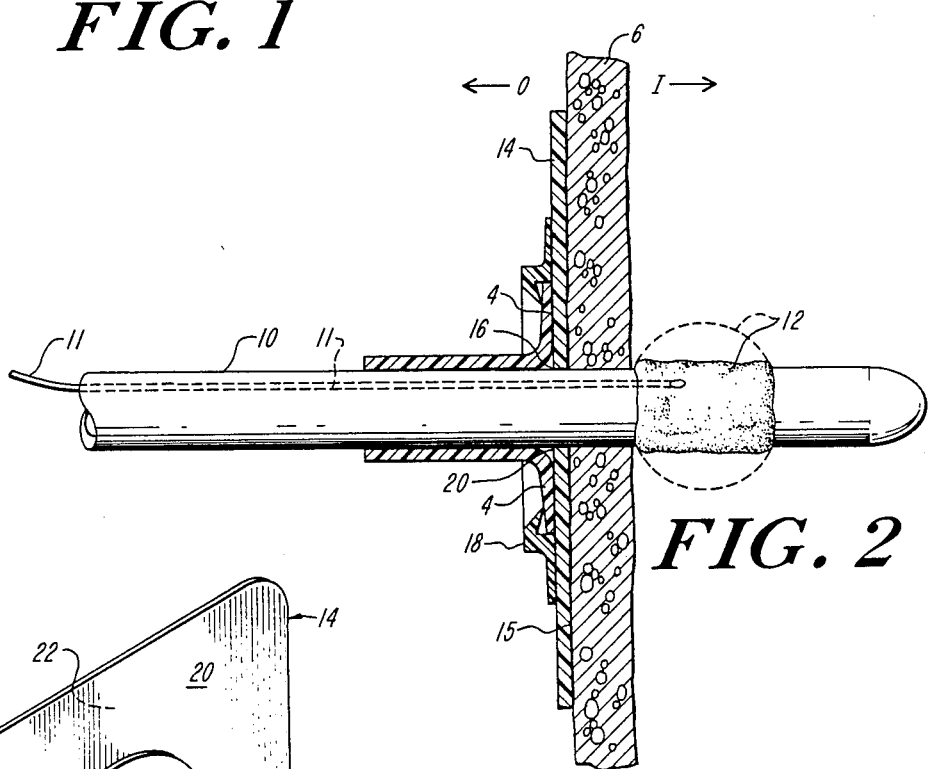
FIG. 2—FIG. 2 is a schematic cross-section showing one embodiment of our invention in use.

In FIG. 2, which shows a schematic cross-section of the apparatus in use, the cooperation of the device with the wafer and the surgical tube is easily seen. In this figure, the patient's skin is indentified by reference character (6). The inside of the patient's body is on the side of the skin identified by the letter "I" and the outside environment is toward the side of the skin identified by the letter "O". First the protective backing is removed from the wafer (14). The tube is inserted through the hole (16) in the wafer. The tube (10) is inserted into the incision, and positioned inside the body as desired. Next, the Foley (a balloon) catheter (12) (shown inflated in phantom), or some other suitable internal anchoring device is inflated through tube (11) or otherwise actuated to prevent the tube from being pulled out of the body. The pectin wafer is threaded onto the tube until it contacts the body, to which it sticks. The interface between the wafer and the patient's skin is indicated by reference character 15. Up until the point, the procedure is known to those skilled in the healing arts and has been described in the above section, Background of the Invention.

After the wafer is applied, our invention is used to secure the tube comfortably and confidently. The surgical tube is inserted into the zig-zag incision (5) along the side of our anchoring device and the anchoring device is threaded along the tube until the anchoring device touches the flange (18) and wafer surface (20). The legs of the anchor are designed so that they snap under the flange (18) of the wafer so that the legs will not pull out even if jostled. Alternatively, while holding the surgical tube to one side, the anchoring device may be snapped into place under the ring, and then the surgical tube may be fitted into the anchoring tube through the zig-zag incision. The surgical tube may be taped to the patient's body to further secure the tube.

Once installed, in conjunction with the flanged pectin wafer and catheter anchoring means (11, 12), our device secures the tube against motion out of the patient's body, or from side to side, thereby insuring that it will not pull loose or become crimped, and thereby minimizing irritation to the patient.

Another embodiment of our invention (not shown) is identical to that shown in FIG. 1, except that it does not include the lenthwise zig-zag incision. With this anchor device the surgical tube is inserted through the support tube, either at the narrow end before the surgical tube is inserted through the wafer and into the body or, at the end nearest the legs, after the tube has been inserted and the pectin wafer has been secured, depending on the type of tube/catheter device used. Otherwise, the procedure is the same as that described with respect to the embodiment of FIG. 1.

Figure 3:
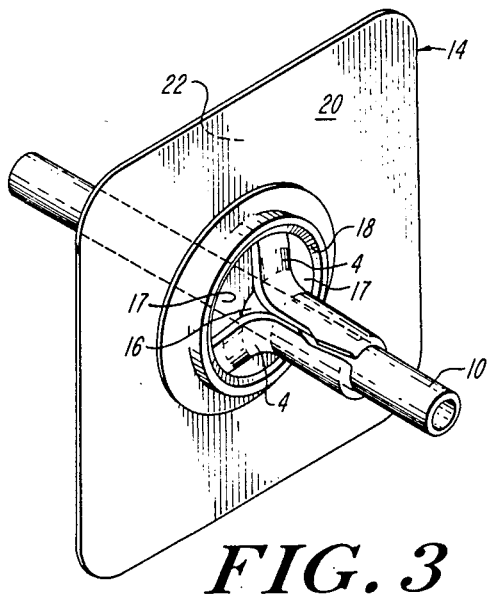
FIG. 3—FIG. 3 is an isometric view of the embodiment of FIG. 1, assembled with a surgical tube and flanged wafer.

A principal feature of our device, most readily understood by reference to FIG. 3, is that the incision site may be inspected without removing the anchor. Visual access to the incision site is provided through the spaces 17 between the legs 4.

Our anchor device may be easily disengaged from its anchoring position to clean the incision interface, the tube and the pectin wafer. The anchor tube may even be completely disengaged from the surgical tube, by unsnapping the legs and feeding the surgical tube back through the zig-zag lengthwise incision (5), or in the case of the embodiment without zig-zag incision, by pulling the device off the end of the tube directed away from the patient. Further, some cleaning may be accomplished through the spaces (17) between the legs (4), without removing the anchor tube. From time to time, the pectin wafer may erode, and must be repaired with a paste. This repair may be easily accomplished by simply disengaging the arms from the flange rim, and sliding the anchor device away from the patient's incision. If the needed repair is slight, it may even be accomplished without removing the anchor. The paste may be applied through the spaces (17) between the legs.

Figure 4:
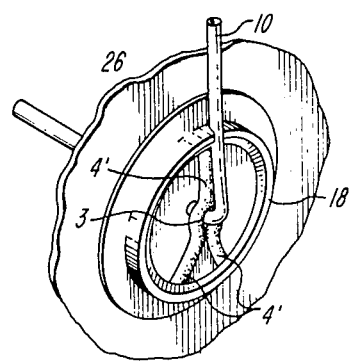
FIG. 4—FIG. 4 is an isometric view of another embodiment of our invention assembled with a smaller diameter surgical tube and flanged wafer.

FIG. 4 shows another embodiment of our invention designed for use with smaller diameter tubes. This device is shaped roughly like a deformed hairpin. Again, three extensions or legs (4') engage the flange (18) of the pectin wafer. The legs define three of the edges of a shallow tetrahedron, intersecting at the apex. At the intersection, the legs meet so that they define a cavity (3) properly sized to accept the tube in use. This embodiment is suitable for use with smaller diameter tubes, where the weight of the tube is not so great that if unsupported, the tube itself would create problems by moving. It is advantageous to cut a small notch (26) in the flange, properly sized to hold the tube by a friction fit. It is also advantageous to size the defined tetrahedron so that sufficient clearance between the apex and the incision site is provided, so that the incision site is visible and may be readily inspected and cleaned, without removing the device.

Our device may be made by various methods familiar to those skilled in the art of medical instrument design. We have used the pectin and polymethycellulose wafer, having a flange bonded to one surface. Wafers of this sort are manufactured by E. R. Squibb & Sons, Inc. of Princeton, N.J., under the trade name "Stomahesive (R) Wafer with Sur-Fit Flange." Hollister Incorporated, of 2000 Hollister Drive, Libertyville, Ill., also manufactures a suitable flanged wafer under the trade name "Two Piece Ostomy System Skin Barrier with Flange." We have fabricated the anchor from a sheet of polycapralactone, a low temperature thermoplastic sold under the tradename Polyform (R), manufactured by: Rolyan Medical Products; Rolyan Manufacturing Company, Inc., Box 555, Menomonee, Wis. 53051. The sheet was heated so that it was soft, rolled into a tube, and then the legs were formed from one end of the tube. Then a zig-zag slot was made in the support tube from end to end.

The embodiment of our device shown in FIG. 4, was made by heating a piece or sheet of polycapralactone material so that it would be maleable, rolling the material around the surgical tube so that a tubular cavity was formed and bending the opposite ends of the stick away from each other so that they extended to the circumference of the flange rim.

Rather than polycapralactone, other suitable thermoplastic materials may be used. Further, our device may also be fabricated by any method known to those skilled in the art of plastic part manufacture, such as injection molding, stamping, extrusion, etc.

It should be understood that the above disclosure is intended to illustrate our device, and should not be considered limiting in many way. Our device may be used in many surgical or medical procedures requiring the stabilization of tubes, or wires. It may be used in the treatment of gastrostomies, as described above, and similarly, may be applied to stabilize other sorts of tubes, including suprapubic tubes, bile tubes, nephrostomy tubes and chest tubes. It may also be used in postoperative continent urostomy and ileostomy procedures, to hold the catheter required to decompress the Koch pouch. It may be used to stabilize a tube cecostomy, a jejunostomy feeding tube, and wound drainage catheter such as Shirley or Chaffin tubes.

Having thus described our invention, We claim:

1. An apparatus for stabilizing surgical tubing, comprising:
   a wafer, having a hole in its center, a first side of said wafer affixed to the patient and a second side of said wafer opposite the first side having a flanged ring concentric with the hole; and
   a support tube through which surgical tubing can be passed, provided at one end with at least three bent legs connected with and extending from said support tube, each leg having edges and a part contiguous to said support tube and an extended part, said contiguous parts extending substantially axially to the support tube, said extended part extending substantailly radially outward from the long axis of the support tube, said legs being shaped such that the edges of said legs at the bends of said legs are equally spaced apart around the perimeter of a circle concentric with said support tube, said legs being flexible and capable of releasably attaching said support tube under a flanged portion of the flanged ring of said wafer, such that when said legs are attached under the flanged ring of said wafer affixed to a patient, a surgical tube passed from an incision in the patient through the hole in said wafer, hole in the flanged ring, and said support tube is secured.

2. The apparatus of claim 1 wherein said supprt tube is formed within a zig-zag incision along its entire length.

3. The apparatus of claim 2, wherein said support tube is cylindrical.

4. The apparatus of claim 3, wherein said support tube comprises a thermoplastic.

5. The apparatus of claim 4 wherein said thermoplastic is polycapralactone.

6. An apparatus for stabilizing surgical tubing, to be used in conjunction with a wafer having a hole in its center and a flanged ring concentric with the hole on a first side of said wafer, a second side of said wafer opposite said firs side being adapted to attach to a portion of a human body, comprising a support tube for receiving surgical tubing, said support tube having at least three bent legs connected with and extending from said support tube to enable said support tube to be attached to the flanged ring on the wafer, each of said legs having edges and a part contiguous to said support tube and an extended part, said contiguous part connecting to said extended part at the bends in said bent legs, and contiguous part extending substantially axially to the support tube, said extended part extending substantially radially outward from the long axis of the support tube, said legs being shaped such that the edges of said legs, at the bends of the legs, are equally spaced apart around the peripmeter of a circle concentric with said support tube, said legs being flexible and of a sufficient length to simultaneously releasably engage the flanged ring of the wafer by snapping under a flanged portion of the flanged ring such that when said apparatus is properly engaged in the wafer and the wafer is secured to a human body, a surgical tube passing from the incision through the hole in the wafer, the hole in the flanged ring and through said support tube is secured, and the support tube rests at a distance from an incision so that the incision may be visually inspected and minor repairs may be made.

7. The apparatus of claim 6, wherein said support tube is formed with a zig-zag incision along its entire length.

8. The apparatus of claim 7, wherein said support tube is a cylinder.

9. The apparatus of claim 8, wherein said support tube comprises a thermoplastic.

10. The apparatus of claim 9 wherein said thermoplastic is polycapralactone.

11. An apparatus for stabilizing surgical tubing, comprising:
   a wafer, having a hole in its center, a first side of said wafer affixed to the patient and a second side of said wafer opposite the first side having a flanged ring concentric with the hole; and
   three legs arranged substantially along three of the edges of a shallow tetrahedron, said legs projecting from a central circular ring segment lying at the apex of said tetrahedron defined by said three legs, said ring segment extending substantailly 120° from any of said three legs, to the next of said three legs, defining a passage for receiving the surgical tubing said legs being flexible and capable of engaging said flanged ring of said wafer by snapping under a flanged portion of the flanged ring to make a surgical tube secure when a surgical tube is passed from a patient's incision through the hole in said wafer, the hole in said flanged ring and through said central circular ring segment.

12. The apparatus of claim 11, wherein said support tube comprises a thermoplastic.

13. The apparatus of claim 12, wherein said thermoplastic is polycapralactone.

14. An apparatus for stabilizing surgical tubing, to be used in conjunction with a wafer, having a hole in its center and a flanged ring concentric with said hole on a first side of said wafer, a second side of said wafer, opposite to said first side of said wafer adapted to attach to a portion of a human body, comprising three legs arranged substantially along three of the edges of a shallow tetrahedron projecting from a central circular ring segment lying at the apex of said tetrahedron defined by said legs, said ring segment extending substantially 120° from any of the three legs to the next of said three legs, defining a passage for receiving the surgical tubing, said legs being flexible and of a sufficient length to simultaneously releasably engage the flanged ring of the wafer by snapping under a flanged portion of the flanged ring such that when said apparatus is properly engaged in said wafer and said wafer is secured to a human body, a surgical tube passing from the patient through the hole in the wafer, the flanged ring and said circular ring segment is secured.

15. The apparatus of claim 14, wherein said apparatus comprises a thermosetting plastic.

16. A method for stabilizing surgical tubing entering the body of a patient through an incision, comprising the steps of
providing a unitary surgical tube/catheter anchoring device;
providing a flanged, adhesive-backed pectin and polymethylcellulose wafer, having a hole of a size suitable to accept the tube arranged concentric with said flange;
arranging the wafer with the adhesive side facing the patient;
guiding the surgical tube/catheter through the hole in the wafer and into the incision;
actuating said catheter anchoring device thereby preventing the catheter from being pulled back through the incision;
adhering the wafer to the patient's skin, said surgical tube/catheter protruding through said hole in said wafer;
providing an apparatus designed to engage said flange, comprising a support tube, for receiving the surgical tubing, said support tube comprising:
at least three bent legs, each of said legs comprising: edges;
a contiguous part to said tube extending substantially axially of said tube; and
an extended part, said extended part extending substantially radially outward from the long axis of said support tube;
said contiguous part connecting to said extended part at the bend;
said legs being of sufficient length to simultaneously releasably engage the flange of the wafer;
said legs being shaped such that the edges of said legs, at the bends of said legs, are spaced apart around the perimeter of a circle concentric with said support tube, so that when installed, visual inspection of the incision may be achieved through the spaces between the edges of the legs;
positioning the surgical tube within the support tube of said apparatus designed to engage said flange; and
simultaneously releasably engaging all of the legs under the flange of the wafer.

17. The method for stabilizing surgical tubing of claim 16 wherein:
said support tube is formed having a lengthwise zig-zag incision along its entire length; and
said positioning of the surgical tube within the support tube of the legged apparatus is accomplished by feeding the surgical tube through said lengthwise zig-zag incision.

18. A method for stabilizing surgical tubing or catheters entering the body of a patient through an incision, comprising the steps of:
providing a wafer, having a hole of a size suitable to accept the tubing and a flange arranged concentric with the hole on a first side of the wafer;
guiding the surgical tubing through the hole in the wafer and into the incision;
securing the surgical tubing in the incision;
adhering a second side of the wafer to the patient, said second side being opposite to the first side of the wafer occupied by the flange, the surgical tubing protruding through the hole in the wafer and thehole in the flange;
providing an apparatus designed to engage the flange comprisng a support tube, for receiving the surgical tubing, said support tube comprising:
at least three bent legs, each of said legs comprising edges;
a contiguous part to said tube extending substantially axially of said tube; and
an extended part, said extended part extending substantially radially outward from the long axis of said support tube;
said contiguous part connecting to said extended part at the bend;
said legs being of sufficient length to simultaneously releasably engage the flange of the wafer;
said legs being shaped such that the edges of said legs, at the bends of said legs, are spaced apart around the perimeter of a circle concentric with said support tube, so that when installed, visual inspection of the incision may be achieved through the spaces between the edges of the legs;
positioning the surgical tubing within the support tube of said apparatus designed to engage the flange; and
engaging the flange with the legs of the apparatus designed to engage the flange.

19. The method of claim 18 wherein the wafer comprises a pectin and polymethylcellulose wafer.

20. The method of claim 18 wherein the wafer is adhered to the patient by an adhesive affixed to the second side of the wafer.

21. The method of claim 18 wherein the step of securing the surgical tubing in the incision is accomplished by providing a unitary surgical tube/catheter anchoring device and actuating said device prior to adhering the wafer to the patient thereby preventing the catheter from being pulled back through the incision.

22. The method of claim 18 wherein the legs of said apparatus designed to engage said flange are engaged to said flange by simultaneously releasably engaging all of the legs under the flange of the wafer.

23. A method for stabilizing surgical tubing or catheters entering the body of a patient through an incision, comprising the steps of:

providing a wafer, having a hole of a size suitable to accept the tubing and a flange arranged concentric with the hole on a first side of the wafer;

guiding the surgical tubing through the hole in the wafer and into the incision;

securing the surgical tubing in the incision;

adhering a second side of the wafer, opposite to the first side of the wafer occupied by the flanged, to the patient, the surgical tubing protruding through the hole in the wafer;

providing an apparatus designed to engage the flange comprising three legs arranged substantially along the three of the edges of a shallow tetrahedron projecting from a central circular ring segment lying at the apex of said tetrahedron defined by said legs, said ring segment extending substantially 120° from any of the three legs to the next of the three legs, defining a passage for receiving the surgical tubing, said legs being flexible and of a sufficient length to simultaneously releasably engage the flange of the wafer such that when said apparatus is properly engaged in said wafer and said wafer is secured to a human body, a surgical tube passing from the patient through the wafer, the flange and the circular ring segment is secured; and engaging the flange with the legs of the apparatus designed to engage the flange.

24. The method of claim 23 wherein the wafer comprises a pectin and polymethylcellulose wafer.

25. The method of claim 23 wherein the wafer is adhered to the patient by an adhesive affixed to the second side of the wafer.

26. The method of claim 23 wherein the step of securing the surgical tubing in the incision is accomplished by providing a unitary surgical tube/catheter anchoring device and actuating said device prior to adhering the wafer to the patient thereby preventing the catheter from being pulled back through the incision.

27. The method of claim 23 wherein the legs of said apparatus designed to engage said flange are engaged to said flange by simultaneously releasably engaging all of the legs under the flange of the wafer.

* * * * *